US00PP30045P3

(12) United States Plant Patent
Eveleens

(10) Patent No.: US PP30,045 P3
(45) Date of Patent: Jan. 1, 2019

(54) ***HYDRANGEA* PLANT NAMED 'HORTMALEGRETTO'**

(50) Latin Name: *Hydrangea macrophylla*
Varietal Denomination: Hortmalegretto

(71) Applicants: Horteve Breeding BV, Aalsmeer (NL); Kolster Holding BV, Boskoop (NL)

(72) Inventor: Cornelis Pieter Eveleens, Aalsmeer (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/731,893

(22) Filed: Aug. 21, 2017

(65) Prior Publication Data

US 2018/0177092 P1 Jun. 21, 2018

(30) Foreign Application Priority Data

Dec. 20, 2016 (QZ) ..... PBR 2016/3228

(51) Int. Cl.
*A01H 5/00* (2018.01)
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea macrophylla* plant named 'Hortmalegretto' that is characterized by its mophead type inflorescences with sterile flower sepals that are bright red in color, its sturdy and thick textured sterile flower sepals, and its good performance as a cut flower.

2 Drawing Sheets

Botanical classification: *Hydrangea macrophylla.*
Varietal denomination: 'Hortmalegretto'.

CROSS REFERENCE TO A RELATED APPLICATION

This application is co-pending with a U.S. Plant patent application filed for a plant derived from the same breeding program that is entitled *Hydrangea* Plant Named 'Hortmagitri' (co-pending U.S. Plant patent application Ser. No. 15/731,894).

BACKGROUND OF THE INVENTION

The present invention relates to a new and distinct cultivar of *Hydrangea macrophylla* and will be referred to hereafter by its cultivar name, 'Hortmalegretto'. 'Hortmalegretto' represents a new big leaf *hydrangea,* a perennial shrub grown for use as a landscape plant and for cut flower production.

'Hortmalegretto' was derived from an ongoing controlled breeding program directed by the Inventor in Boskoop, The Netherlands. The objective of the breeding program was to develop new cultivars of *Hydrangea* with flowers that are red in color. 'Hortmalegretto' arose from a controlled cross made by the Inventor in June of 2009 between unnamed and unpatented proprietary plants in the Inventor's breeding program; reference no. 08-010-03 as the female parent and reference no. 08-016-03 as the male parent. 'Hortmalegretto' was selected as a single unique plant from amongst the resulting seedlings in August of 2013.

Asexual propagation of the new cultivar was first accomplished by stem cuttings by the Inventor in Boskoop, The Netherlands in August of 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hortmalegretto' as a unique cultivar of *Hydrangea macrophylla.*

1. 'Hortmalegretto' exhibits mophead type inflorescences with sterile flower sepals that are bright red in color.
2. 'Hortmalegretto' exhibits sturdy and thick textured sterile flower sepals.
3. 'Hortmalegretto' performs well as a cut flower.

The female parent of 'Hortmalegretto' differs from 'Hortmalegretto' in having sterile flower sepals that are dark pink in color. The male parent of 'Hortmalegretto' differs from 'Hortmalegretto' in having a less vigorous growth habit and inflorescences that are smaller in size. 'Hortmalegretto' can be most closely compared to the *Hydrangea macrophylla* cultivars 'Kolmaru' (U.S. Plant Pat. No. 25,104) and 'Hortmagitri'. 'Kolmaru' is similar to 'Hortmalegretto' in having inflorescences with sterile sepals that is red in color. 'Kolmaru' differs from 'Hortmalegretto' in having sterile flower sepals that are darker red in color and less sturdy and thick textured and in having leaves that are darker green in color. 'Hortmagitri' is similar to 'Hortmalegretto' in having inflorescences with sterile sepals that are red in color and thick textured. 'Hortmagitri' differs from 'Hortmalegretto' in having sterile sepals that are darker red in color with even darker red markings.

BRIEF DESCRIPTION OF THE DRAWINGS

The accompanying colored photographs illustrate the overall appearance and distinct characteristics of the new *Hydrangea*. The photographs were taken of a plant two years in age as grown in a 17-cm container in a greenhouse in Boskoop, The Netherlands.

The photograph in FIG. 1 provides a side view of the plant habit of 'Hortmalegretto' in bloom.

Figure 1:
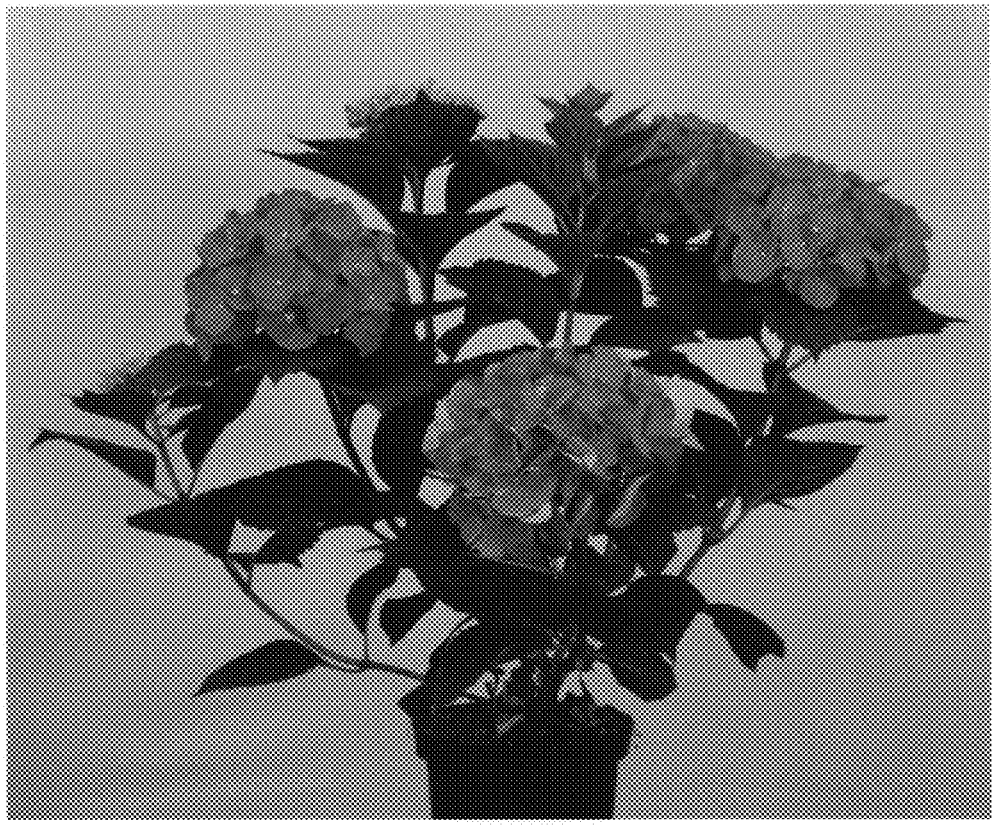
Figure 2:
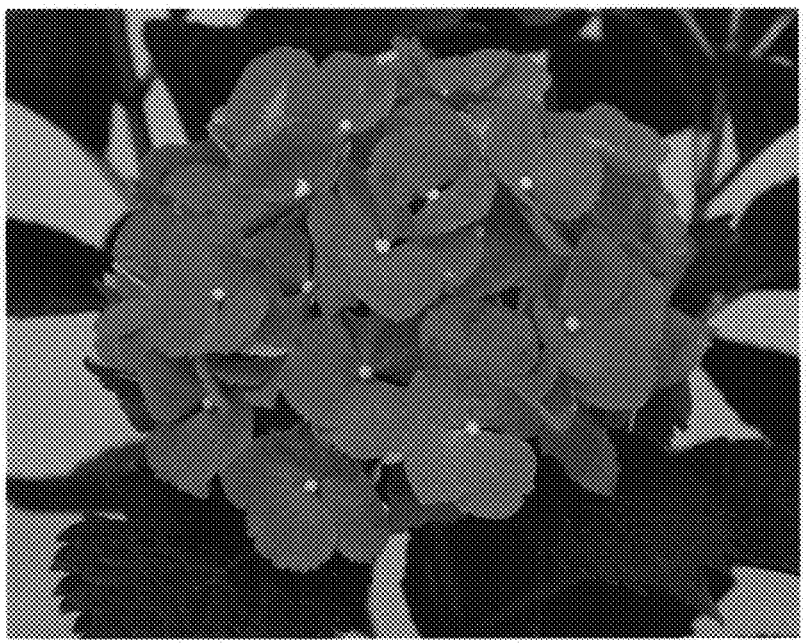

The photograph in FIG. 2 provides a close-up view of an inflorescence of 'Hortmalegretto'.

Figure 3:
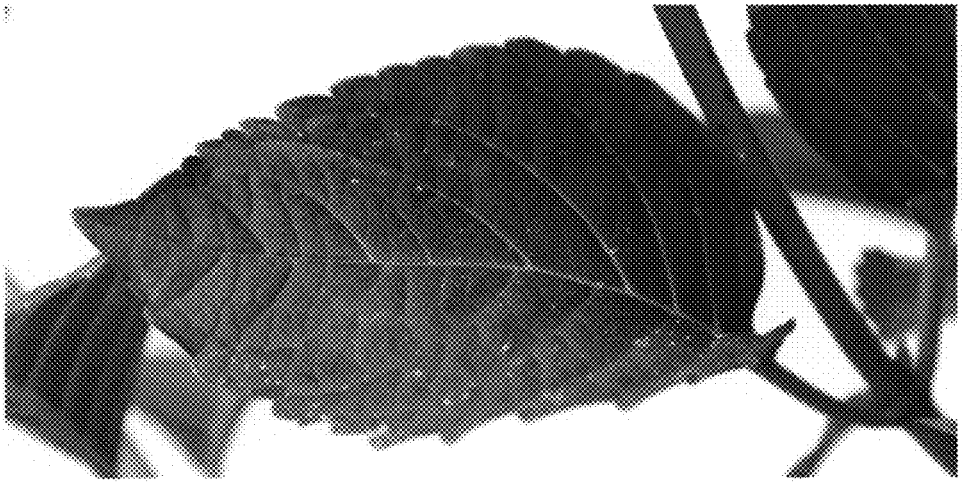

The photograph in FIG. 3 provides a close-up view of a leaf of 'Hortmalegretto'. The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown in 17-cm containers in a greenhouse in in June in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—From late summer to fall; showy for at least 2 months in The Netherlands.

*Plant type.*—Perennial shrub, mophead type *Hydrangea.*

*Plant habit.*—Broadly spreading to upright.

*Height and spread.*—An average of 56.6 cm in height and 76.3 cm in spread and about 1 m in height and width as a 3 year-old plant in the landscape.

*Hardiness.*—At least in U.S.D.A. Zones 5 to 9.

*Diseases and pests.*—No susceptibility or resistance to pests and diseases has been observed.

*Root description.*—Fibrous and fine, 199D in color.

*Propagation.*—Stem cuttings.

*Time required for root development.*—An average of 3.5 weeks for root initiation with a young rooted plant produced in an average of six months.

*Growth rate.*—Moderate.

Stem description:

*Stem shape.*—Rounded.

*Stem strength.*—Strong.

*Stem aspect.*—Upright to an average angle of 55° to soil.

*Stem color.*—Immature stems; 144B, mature stems; 144A, flushed with 176B, older bark; 199C to 199D.

*Stem size.*—An average of 46.7 cm (excluding the inflorescence) in length and 8 mm in diameter.

*Stem surface.*—Immature and mature stems; glabrous and sparsely lenticellate with lenticels; an average of 1.5 mm in length, 0.5 mm in width, 187A to N187B in color.

*Branching.*—Freely branched with an average of 7 lateral branches, branching improves with pinching.

*Internode length.*—An average of 7.4 cm.

Foliage description:

*Leaf shape.*—Broadly ovate to broadly elliptic.

*Leaf arrangement.*—Opposite.

*Leaf division.*—Simple.

*Leaf number.*—An average of 10 (5 pairs) per lateral branch.

*Leaf base.*—Short attenuate.

*Leaf apex.*—Apiculate.

*Leaf margins.*—Serrate.

*Leaf venation.*—Pinnate, color; upper surface 144A, lower surface 144B to 144C, lower surface main veins are covered with short hairs; an average of 0.4 mm in length, too small to measure color.

*Leaf size.*—An average of 14.2 cm in length and 11.5 cm in width.

*Leaf attachment.*—Petiolate.

*Leaf surface.*—Upper and lower surfaces; smooth and slightly rugose.

*Leaf color.*—Young leaves upper surface between NN137A and 147A, young lower surface between 138B and 147B, mature upper surface 144A, mature lower surface 144B to 144C.

*Petioles.*—An average of 2.7 cm in length and 4 mm in diameter, color upper and lower surface 144A, surface; smooth and slightly glossy, strong.

Inflorescence description:

*Inflorescence type.*—Flattened globular, mophead type, compound corymb of rotate-shaped sterile flowers over fertile flowers.

*Lastingness of inflorescence.*—Sterile flowers; an average of 6 weeks, persistent, fertile flowers; an average of 5 days, self-cleaning.

*Lastingness as a cut flower.*—About 2 weeks in full color, longer as a drying inflorescence.

*Inflorescence number.*—One per lateral stem.

*Inflorescence size.*—An average of 11.5 cm in height and 18.6 cm in diameter.

*Flower number.*—An average of 150 sterile flowers and 55 fertile flowers per inflorescence.

*Flower fragrance.*—None.

*Flower aspect.*—Sterile flowers; upright, outwards, and slightly drooping, fertile flowers; upright.

*Flower size.*—Sterile flowers; an average of 4.5 cm in diameter and 2.3 cm in depth, fertile flowers; an average of 1.3 mm in diameter and 9 mm in depth.

*Flower shape.*—Sterile flowers; rotate, fertile flowers; rotate, petals drop when maturing.

*Flower buds.*—Sterile flowers; an average of 3 mm in length, 4 mm in diameter, flattened globular in shape, color; 68C to 68D, fertile flowers; an average of 6 mm in length and 4 mm in diameter, obovate in shape, color; 145B, top flushed with 58D, base 145A.

*Peduncles.*—An average of 10 cm in length and 8 mm in diameter, held upright to outwards, 63C to 63D in color, smooth surface, strong.

*Pedicels.*—Sterile flowers; an average of 2.8 cm in length and 2 mm in diameter, held at an average angle of 45° to peduncle, 63A to 63B in color, moderate strength, dull surface is moderately covered with thin hairs; an average of 0.2 mm in length and too small to measure color, fertile flowers; an average of 3 mm in length and 1 mm in diameter, held at an average angle of 20° to vertical, 63C to 63D in color, moderate strength, dull surface moderately covered with thin pubescence 0.2 mm in length and too small to measure color.

*Petals.*—Sterile flowers; average of 4, occasionally 5, rotate, ovate in shape, concave, acute apex, cuneate base, entire margin, an average of 5 mm in length and 2.5 mm in width, glabrous and dull upper and lower surfaces, color when opening upper surface 75B, margins NN155D, color when opening lower surface 70D, margins NN155D, color when fully open upper surface 75B with margins NN155D, color when fully open lower surface 70D with margins NN155D, fertile flowers; average of 4, occasionally 5, rotate, ovate in shape, concave, acute apex, cuneate base, entire margin, an average of 5 mm in length and 3 mm in width, glabrous and dull upper and lower surfaces, color when opening upper surface 68B, margins NN155B, color when opening lower surface 68C to 68D, margins N155B, color when fully open upper surface 68B, margins N155B, color when fully open lower surface 68D, margins N155B.

*Sepals.*—Sterile flowers; an average of 4, occasionally 5, rotate in arrangement, near deltoid to broad ovate and rhomboidal in shape, apex is bluntly acute, cuneate base, margin entire to slightly irregularly dentate to serrate, an average of 2.6 cm in length and 3 cm in width, color; upper surface when opening N57A, lower surface when opening N57C, upper surface when fully open between 58A and 63A, fading to 60A to 60B, strongly flushed with 147A, lower surface when fully open between 59D, fading to 63B, strongly flushed with 148B, both surfaces glabrous and dull, fertile flowers; an average of 6, occasionally 5, rotate in arrangement, ovate in shape, acute apex, broadly cuneate base, entire margin, an average of 1 mm in length and width, color when opening upper surface 145B to 145C, flushed with 68A, color when opening lower surface 145B to 145C, flushed with 68A, color when fully open upper and lower surface, 145B to 145C, flushed with 68A, both surfaces glabrous and dull.

Reproductive organs:

*Gynoecium.*—Sterile flowers; 3, occasionally 4 pistils, an average of 1.5 mm in length, stigma; club-shaped and NN155A in color, style; 1 mm in length, N155B in color, ovary is 157D in color, fertile flowers; an average of 3 pistils, occasionally 4; an average of 1.5 mm in length, stigma; club-shaped and NN155A in color, style; 1 mm in length, N155A in color, ovary is 150D in color.

*Androecium.*—Sterile flowers; an average of 8 stamens, filaments; an average of 3 mm in length and N155C in color, anthers; oblong in shape, an average of 1 mm in length and 155A in color, pollen; moderate in quantity, 159D in color, fertile flowers; an average of 10 stamens, filaments; an average of 3 mm in length and NN155D in color, anthers; oblong in shape, an average of 1 mm in length and 157D in color, pollen; moderate in quantity and 159D in color.

*Fruit and seed.*—None observed to date.

It is claimed:

1. A new and distinct cultivar of *Hydrangea* plant named 'Hortmalegretto' substantially as herein illustrated and described.

* * * * *